United States Patent [19]

(12) United States Patent
Kim et al.

(10) Patent No.: US 11,089,976 B2
(45) Date of Patent: Aug. 17, 2021

(54) METHOD AND APPARATUS FOR ASSISTING SPASTICITY AND CLONUS EVALUATION USING INERTIAL SENSOR

(71) Applicant: Daegu Gyeongbuk Institute of Science and Technology, Daegu (KR)

(72) Inventors: Jong Hyun Kim, Daegu (KR); Seo Young Choi, Daegu (KR); Yong Beom Shin, Busan (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 873 days.

(21) Appl. No.: 15/239,253

(22) Filed: Aug. 17, 2016

(65) Prior Publication Data

US 2017/0049363 A1 Feb. 23, 2017

(30) Foreign Application Priority Data

Aug. 19, 2015 (KR) .......................... 10-2015-0116796

(51) Int. Cl.
*A61B 5/11* (2006.01)
*A61B 5/00* (2006.01)
(52) U.S. Cl.
CPC .......... *A61B 5/1107* (2013.01); *A61B 5/4082* (2013.01); *A61B 5/4519* (2013.01); *A61B 5/486* (2013.01); *A61B 5/1121* (2013.01); *A61B 5/7271* (2013.01); *A61B 5/7278* (2013.01); *A61B 5/743* (2013.01); *A61B 2562/0219* (2013.01)

(58) Field of Classification Search
CPC .................................................. A61B 5/1107
See application file for complete search history.

(56) References Cited

U.S. PATENT DOCUMENTS

2009/0118649 A1   5/2009  Cabrera et al.
2012/0278024 A1*  11/2012  Lee .................. G01C 21/16
                                                         702/87

FOREIGN PATENT DOCUMENTS

KR          10-1528183 B1     6/2015

OTHER PUBLICATIONS

Office Action dated Oct. 26, 2016 in KR Application No. 10-2015-0116796.
Choi, Seoyoung, "IMU-based Assessment of Knee Spasticity to Improve Reliability of Modified Tardieu Scale in Cerebral Palsy," Masters Thesis, Department of Robotics Engineering, DGIST, 2015, 33 pgs.

* cited by examiner

*Primary Examiner* — Daniel L Cerioni
*Assistant Examiner* — Yasmeen S Warsi
(74) *Attorney, Agent, or Firm* — Harness, Dickey & Pierce, P.L.C.

(57) ABSTRACT

Provided is a method and apparatus for assisting spasticity and clonus evaluation using an inertia sensor, the apparatus including an acquirer configured to acquire a measured value from an inertia sensor attached to an object, a calculator configured to calculate an angle of a joint of the object based on the measured value, and a processor configured to evaluate a spasticity and a clonus based on the angle of the joint.

8 Claims, 6 Drawing Sheets

METHOD AND APPARATUS FOR ASSISTING SPASTICITY AND CLONUS EVALUATION USING INERTIAL SENSOR

CROSS-REFERENCE TO RELATED APPLICATION(S)

This application claims the priority benefit of Korean Patent Application No. 10-2015-0116796 filed on Aug. 19, 2015, in the Korean Intellectual Property Office, the disclosure of which is incorporated herein by reference for all purposes.

BACKGROUND

1. Field

One or more example embodiments relate to a method and apparatus for assisting spasticity evaluation using an inertia sensor attached to an object by calculating an angle of a joint of the object based on an acquired measured value, measuring the angle of the object, providing a visual biofeedback on a movement of the joint in real time, and assisting reliable spasticity evaluation on the joint.

2. Description of Related Art

An upper motor neuron syndrome may be an abnormality in mobility control that occurs due to an injury of a central nervous system including a brain and a spinal cord. A spasticity and a clonus may be a symptom of the upper motor neuron syndrome. The spasticity and the clonus may result from an abnormal overexcitability and adversely affect a voluntary movement.

The spasticity may occur when a joint is passively stretched by a rater. In this instance, the stretch reflex may be overexcited based on a moving velocity of the joint, which may increase a muscular tension. As a degree of spasticity increases, susceptibility for the velocity and the muscular tension may also increase.

Also, the clonus may occur due to the overexcitability in the stretch reflex and accompany a continuous tremor.

Various spasticity evaluations have been performed based on such characteristics of spasticity. The spasticity evaluations may include, for example, a modified Tardieu scale (MTS) and a modified Ashworth scale (MAS). The MTS may be applied to a spasticity evaluation in a hospital. In the MTS, the spasticity and the clonus may be evaluated based on a characteristic that a muscular tension rapidly increases dependently on the velocity.

However, the velocity and the measured value may vary based on a subjective sense of a user during the measurement and thus, the spasticity and clonus evaluation performed based on the varying measured value may have insufficient consistency, reliability, and objectivity.

Accordingly, there is desire for technology for reliably evaluating a spasticity and a clonus.

SUMMARY

An aspect provides a method and apparatus to calculate an angle of a joint of an object based on a measured value, for example, an acceleration and an angular velocity using an inertia sensor attached to the object and evaluate a spasticity and a clonus of the joint may be evaluated based on the angle of the joint to accurately acquire the angle of the joint based on objective numerical values, thereby achieving a high reliability of a spasticity evaluation based on the angle of the joint.

Another aspect also provides a method and apparatus to acquire an acceleration from an acceleration meter included in the inertia sensor and the angular velocity from an angular velocity meter included in the inertia sensor, calculate the angle of the joint based on the acceleration in response to a determination that an object is in a quasi-static state when a variation in each of the acceleration and the angular velocity is less than a first set value, for example, when little variation is present, and calculate the angle of the joint based on the angular velocity in response to a determination that the object is in a dynamic state when the variation in each of the acceleration and the angular velocity is greater than or equal to a second set value, for example, the variation is relatively large such that the angle of the joint is accurately acquired based on objective numerical values acquired from the inertia sensor irrespective of a state of the object.

Still another aspect also provides a method and apparatus to provide a visual biofeedback on a velocity using an angular velocity of an inertia sensor in real time by displaying the velocity on a screen and allow a velocity adjustment while an angle of a joint of an object is measured so as to support objective velocity adjustment independently of a subjective sense and an experience of a user.

According to an aspect, there is provided an apparatus for assisting spasticity evaluation using an inertia sensor, the apparatus including an acquirer configured to acquire a measured value from an inertia sensor attached to an object, a calculator configured to calculate an angle of a joint of the object based on the measured value, wherein the calculator is configured to calculate a gradient relative to a ground based on a magnitude of an acceleration with respect to a gravitational acceleration as the angle of the joint when the acquired measured value is the acceleration, and, the calculator is configured to calculate the angle of the joint by integrating an angular velocity when the acquired measured value is the angular velocity, and a processor configured to evaluate a spasticity and a clonus of the joint based on the angle of the joint.

According to another aspect, there is also provided a method of assisting spasticity evaluation using an inertia sensor, the method including acquiring a measured value from an inertia sensor attached to an object, calculating an angle of a joint of the object based on the measured value, the calculating including calculating a gradient relative to a ground based on a magnitude of an acceleration with respect to a gravitational acceleration as the angle of the joint when the acquired measured value is the acceleration and calculating the angle of the joint by integrating an angular velocity when the acquired measured value is the angular velocity, and evaluating a spasticity and a clonus of the joint based on the angle of the joint.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

In the present disclosure, there is a method and apparatus for assisting spasticity and clonus evaluation using an inertia sensor. In this disclosure, the inertia sensor may be used to perform the spasticity and clonus evaluation not limited to a modified Tardieu scale (MTS) but based on characteristics of a spasticity and a clonus with increased reliability and objectivity when compared to a typical spasticity and clonus evaluation. The method may be applicable to a measurement of the clonus as well as the spasticity.

Figure 1:
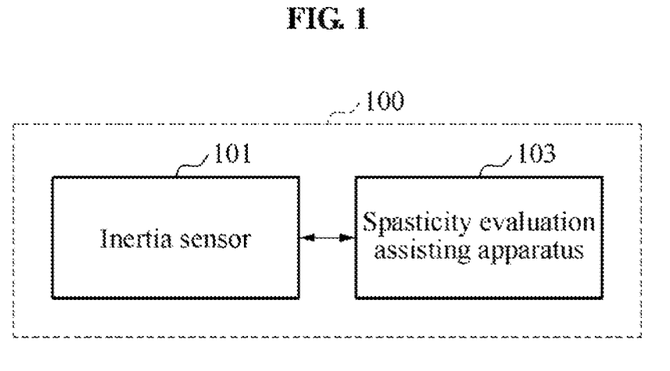
FIG. 1 is a block diagram illustrating an overall system including an apparatus for assisting spasticity evaluation using an inertial sensor according to an example embodiment.

FIG. 1 is a block diagram illustrating an overall system including an apparatus for assisting spasticity evaluation using an inertial sensor according to an example embodiment. Hereinafter, the apparatus for assisting spasticity evaluation using an inertia sensor may also be referred to as, for example, a spasticity evaluation assisting apparatus.

Referring to FIG. 1, an overall system 100 may include an inertia sensor 101 and an apparatus 103 for assisting spasticity evaluation using the inertia sensor 101.

The inertia sensor 101 may be an inertial measurement unit (IMU) and attached to an object, for example, a human body. The inertia sensor 101 may measure a measured value based on a movement of the object. Here, the inertia sensor 101 may include, for example, at least one of an acceleration meter, for example, an accelerometer and an angular velocity meter, for example, a gyroscope.

The apparatus 103 may calculate an angle of a joint of the object based on the measured value acquired from the inertia sensor 101, and evaluate a spasticity and a clonus of the joint based on the angle of the joint.

In this example, the apparatus 103 may use an accurate angle of the joint acquired based on objective numerical values to evaluate the spasticity and the clonus of the joint so as to increase reliability on the spasticity evaluation.

Also, the apparatus 103 may provide an evaluation result of the spasticity and the clonus such that a severity of brain injury is accurately acquired.

The apparatus 103 may be an apparatus for assisting evaluation with increased reliability and objectivity using the inertia sensor when compared to a typical evaluation in lieu of an apparatus for directly acquiring an evaluation result from a spasticity evaluation.

Figure 2:
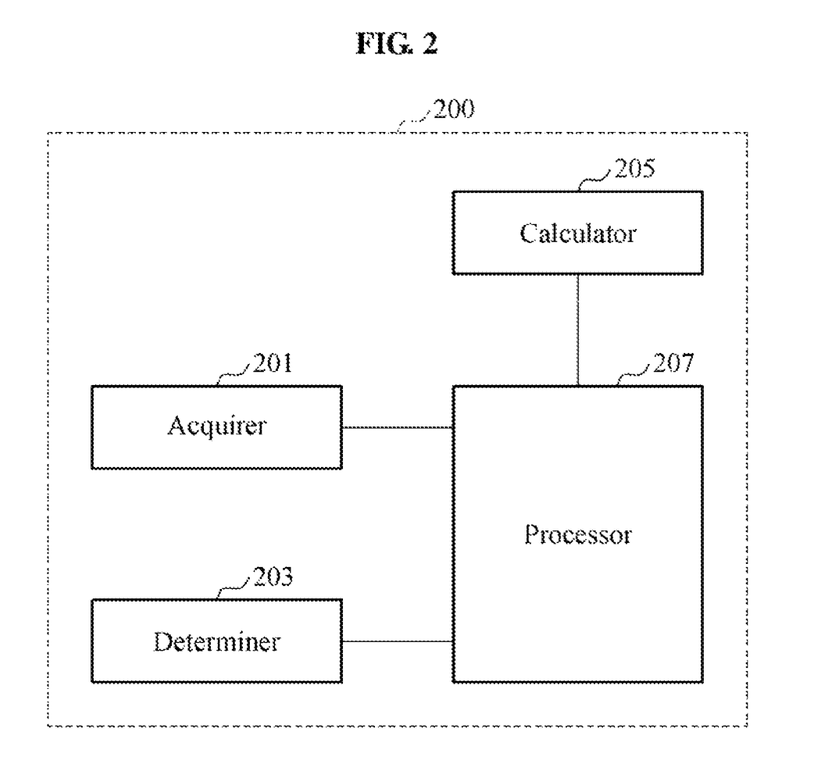
FIG. 2 is a block diagram illustrating an apparatus for assisting spasticity evaluation using an inertial sensor according to an example embodiment.

FIG. 2 is a block diagram illustrating an apparatus for assisting spasticity evaluation using an inertial sensor according to an example embodiment.

Referring to FIG. 2, an apparatus 200 for assisting spasticity evaluation using an inertia sensor may include an acquirer 201, a determiner 203, a calculator 205, and a processor 207.

The acquirer 201 may acquire a measured value from an inertia sensor attached to an object, for example, a human body. Here, the inertia sensor may include an acceleration meter and an angular velocity meter to measure an acceleration and an angular velocity based on a movement of the object as the measured value. In this example, a plurality of inertia sensors may be attached to predetermined portions spaced apart relative to a joint of the object to sense the movement of the object.

For example, the acquirer 201 may acquire the acceleration from the acceleration meter included in the inertia sensor and acquire the angular meter included in the inertia sensor.

Also, the acquirer 201 may acquire the acceleration from the acceleration meter included in the inertia sensor when the object is in a quasi-static state and acquire the angular velocity from the angular velocity meter included in the inertia sensor when the object is in a dynamic state.

When the plurality of inertia sensors is attached to the object, the acquirer 201 may control the acceleration meter or the angular velocity meter included in each of the plurality of inertia sensors to acquire the measured value from the plurality of inertia sensors. For example, the acquirer 201 may activate acceleration meters included in the plurality of inertia sensors and acquire the acceleration for calculating a stop angle of the joint from at least a portion of the activated acceleration meters. Also, the acquirer 201 may activate angular velocity meters included in the plurality of inertia sensors and acquire the angular velocity for calculating a moving angle of the joint from at least a portion of the activated angular velocity meters.

The determiner 203 may determine that the object is in the quasi-static state when all movements sensed in the plurality of inertia sensors are less than a set value. Also, the determiner 203 may determine that the object is in the dynamic state when a movement sensed in one of the plurality of inertia sensors is greater than or equal to the set value. In this example, when a variation in each of the acceleration and the angular velocity is less than a first set value, for example, when little variation is present, the determiner 203 may determine that the object is in the quasi-static state. Also, when the variation in each of the acceleration and the angular velocity is greater than or equal to a second set value, for example, when a relatively great variation is present, the determiner 203 may determine that the object is in the dynamic state.

The calculator 205 may calculate the angle of the joint of the object based on the measured value acquired from the inertial sensor of the acquirer 201 so as to accurately acquire the angle of the joint based on objective numerical values. In this example, in response to a determination that the object is in the quasi-static state, the calculator 205 may calculate the angle of the joint of the object based on the acceleration acquired from the acceleration meter in the inertia sensor. Also, in response to a determination that the object is in the dynamic state, the calculator 205 may calculate the angle of the joint of the object based on the angular velocity acquired from the angular velocity meter in the inertia sensor.

When the acquired measured value is the acceleration, the calculator 205 may calculate a gradient relative to a ground based on a magnitude of the acceleration with respect to a gravitational acceleration. When the acquired measured value is the angular velocity, the calculator 205 may calculate the angle of the joint by integrating the angular velocity.

The processor 207 may evaluate a spasticity and a clonus of the joint based on the angle of the joint. The processor 207 may evaluate the spasticity and the clonus by obtaining at least one of a sum of stop angles, for example, at least one angle, of the joint calculated when the object is in the quasi-static state and a sum of moving angles, for example, a plurality of moving angles acquired at a preset interval, of the joint calculated when the object is in the dynamic state.

In the evaluation of the spasticity and the clonus, the processor 207 may not directly evaluate the spasticity and the clonus. Instead, the processor 207 may complement a subjective portion using the inertia sensor to support a user to objectively perform measurement and increase reliability.

Also, the processor 207 may provide a real-time visual biofeedback on the angular velocity of the joint using the inertia sensor. To this end, the plurality of inertia sensors may be attached to the predetermined portions spaced apart relative to the joint. The acquirer 201 may acquire the angular velocity from the angular velocity meter included in each of the plurality of inertia sensors.

The processor 207 may provide the real-time visual biofeedback by displaying a joint angular velocity obtained by calculating a sum of the acquired angular velocities on a screen.

Figure 3:
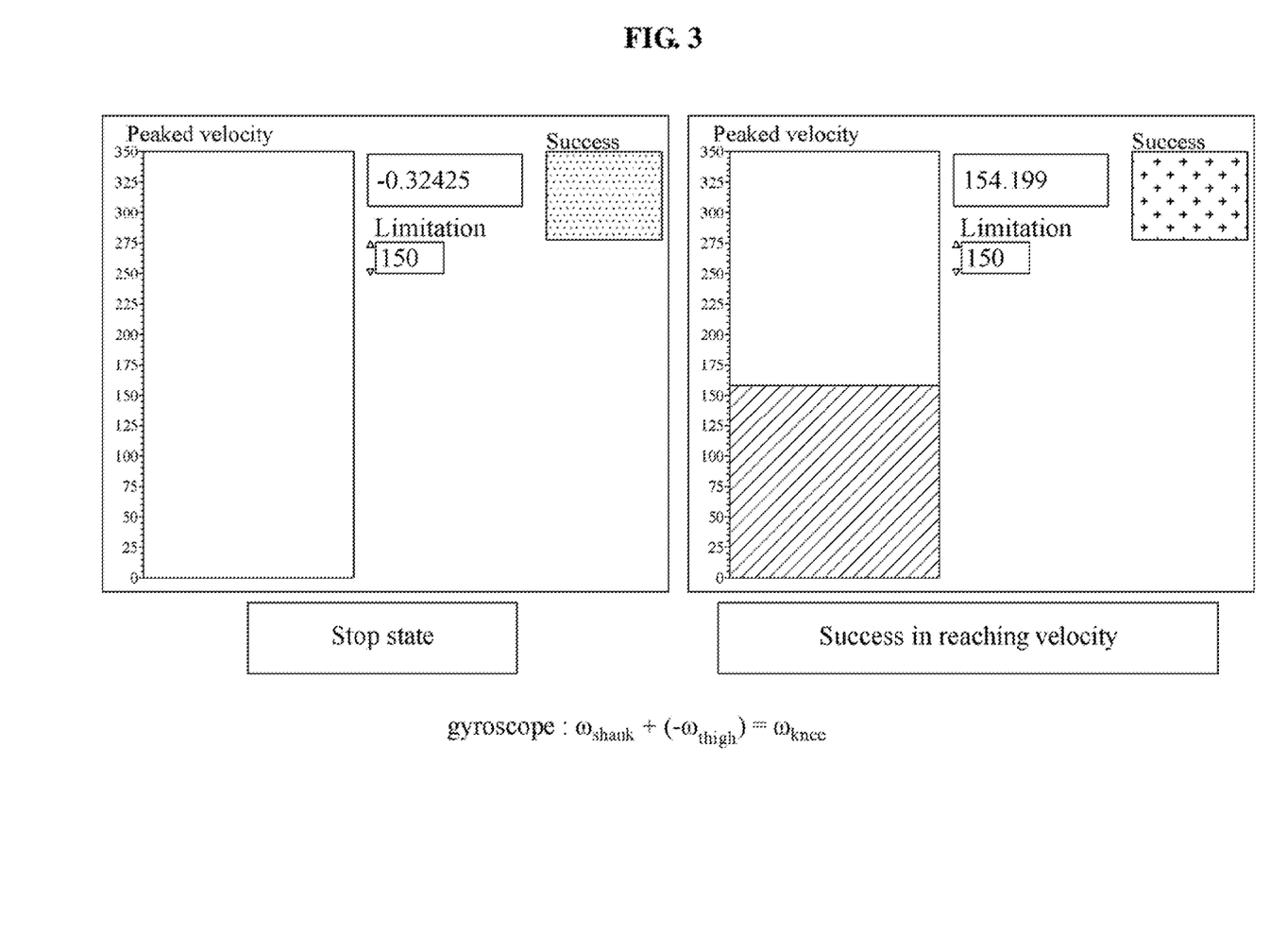
FIG. 3 is a diagram illustrating an example of an image provided as a visual biofeedback on a joint angular velocity according to an example embodiment.

FIG. 3 is a diagram illustrating an example of an image provided as a visual biofeedback on a joint angular velocity according to an example embodiment.

Referring to FIG. 3, the processor 207 may provide an object visual biofeedback by displaying a comparison between a quasi-static state of an object and a state of a success in reaching a joint angular velocity acquired through evaluation, for example, a success in reaching a target velocity on a screen. By providing a real-time visual biofeedback on an angular velocity of a joint using an inertia sensor, the processor 207 may increase reliability on evaluation of a user.

In this example, the angular velocity may be acquired in real time from the angular velocity meter of the inertia sensor attached to the joint and a joint angular velocity obtained by summating angular velocities of joints may be displayed on a screen. Thereafter, a velocity adjustment may be performed.

The processor 207 may use an accurate angle of the joint acquired based on objective numerical values to evaluate a spasticity and a clonus of the joint so as to increase reliability on the spasticity evaluation.

The processor 207 may provide an evaluation result of the spasticity and the clonus such that a severity of brain injury is accurately acquired.

The processor 207 may provide medical care information based on the evaluation result of the spasticity and the clonus. For example, the processor 207 may provide information on, for example, medication with Baclofen and Botulinum toxin injection based on an evaluation result of the spasticity and the clonus.

The apparatus 200 may acquire the angular velocity from the angular velocity meter of the inertia sensor in real time and display a moving velocity to be measured on a screen. Also, the apparatus 200 may provide a visual biofeedback on the measured velocity such that the moving velocity of the joint is to be adjusted. Through this, the moving velocity may be objectively adjusted and measured in a spasticity evaluation having a velocity-dependent characteristic.

Figure 4:
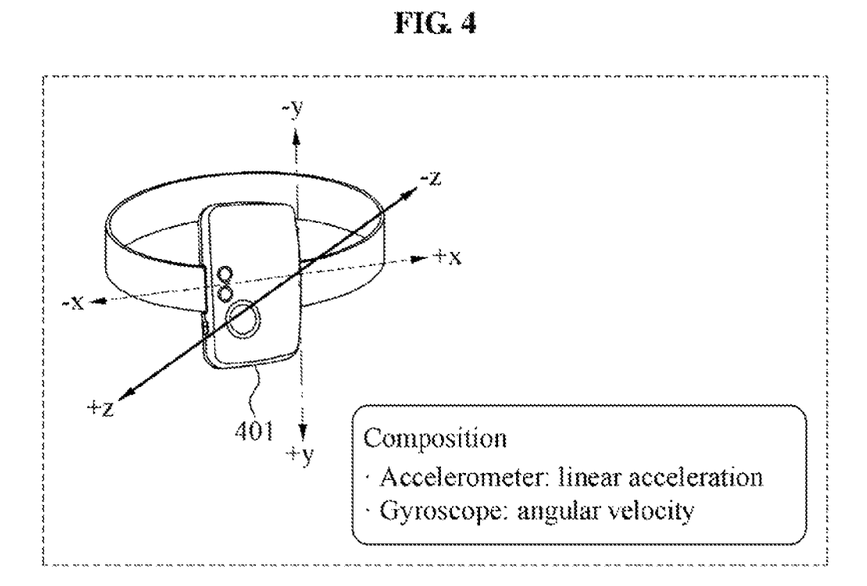
FIG. 4 is a diagram illustrating an example of an inertia sensor providing a measured value to an apparatus for assisting spasticity evaluation using the inertia sensor according to an example embodiment.

FIG. 4 is a diagram illustrating an example of an inertia sensor providing a measured value to an apparatus for assisting spasticity evaluation using the inertia sensor according to an example embodiment.

Referring to FIG. 4, an inertia sensor 401 may be attached to an object using a band to measure a measured value based on a movement of the object. Here, the inertia sensor 401 may include, for example, at least one of an acceleration meter and an angular velocity meter.

The inertia sensor 401 may measure an acceleration as the measured value using an acceleration meter included in the inertia sensor 401. The inertia sensor 401 may measure an angular velocity as the measured value using an angular velocity meter included in the inertia sensor 401.

The inertia sensor 401 may also include a wireless communicator, for example, Bluetooth. Through the wireless communicator, the inertia sensor 401 may transmit the measured value to an apparatus for assisting spasticity evaluation using an inertia sensor.

Figure 5:
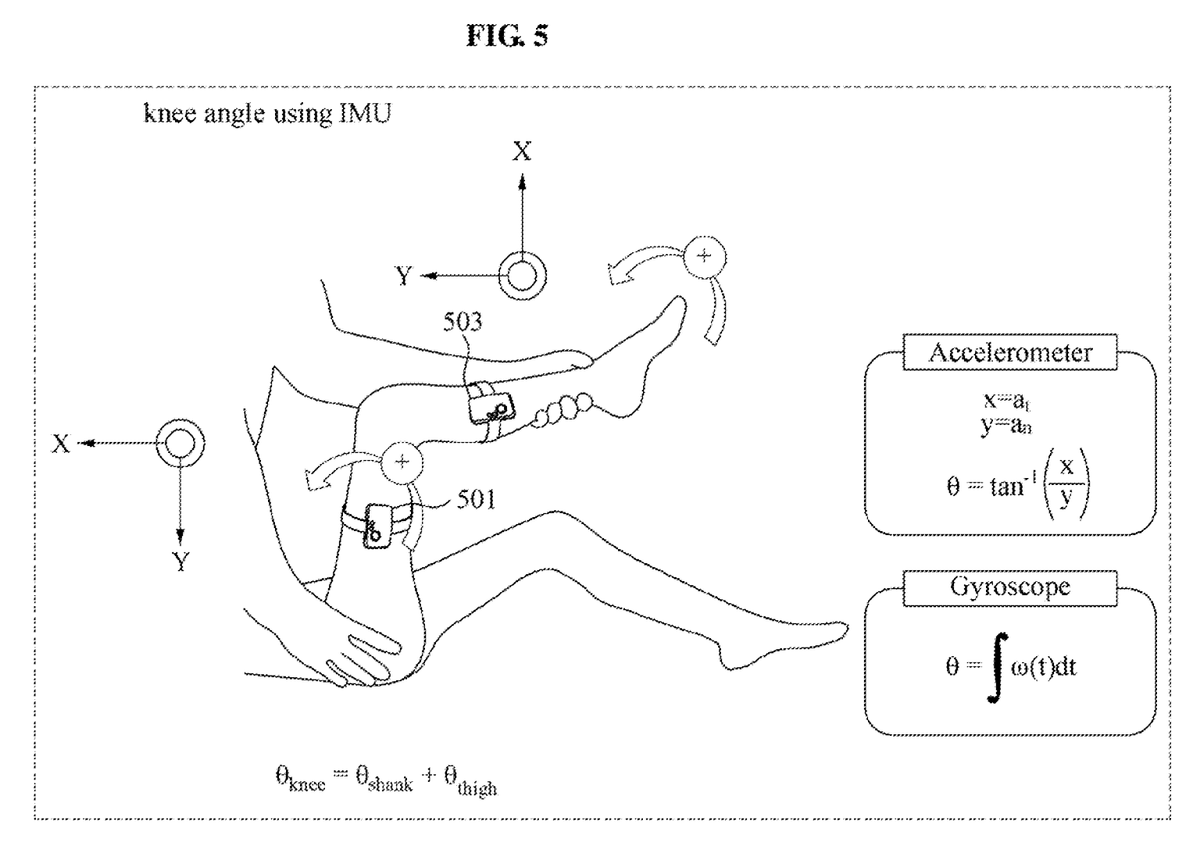
FIG. 5 is a diagram illustrating an example of spasticity evaluation performed in an apparatus for assisting spasticity evaluation using an inertia sensor according to an example embodiment.

FIG. 5 is a diagram illustrating an example of spasticity evaluation performed in an apparatus for assisting spasticity evaluation using an inertia sensor according to an example embodiment.

Referring to FIG. 5, a plurality of inertia sensors may be attached to predetermined portions spaced apart relative to a joint of an object to sense a movement of the object. For example, a first inertia sensor 501 and a second inertia sensor 503 may be respectively attached to a thigh part and a shank part spaced apart from each other relative to a knee joint.

The spasticity evaluation assisting apparatus may determine that the object is in a quasi-static state when all movements sensed by the first inertia sensor 501 and the second inertia sensor 503 are less than a set value. The spasticity evaluation assisting apparatus may determine that the object is in a dynamic state when a movement sensed by one of the first inertia sensor 501 and the second inertia sensor 503 is greater than or equal to a set value.

In response to a determination that the object is in the quasi-static state, the spasticity evaluation assisting apparatus may activate acceleration meters included in the first inertia sensor 501 and the second inertia sensor 503, and acquire accelerations for calculating a stop angle of the knee joint from at least a portion of the activated acceleration meters. For example, the spasticity evaluation assisting apparatus may acquire a first acceleration measured by the first inertia sensor 501 at the thigh part and a second acceleration measured by the second inertia sensor 503 at the shaft part. Also, in response to a determination that the object is in the dynamic state, the spasticity evaluation assisting apparatus may activate angular velocity meters included in the first inertia sensor 501 and the second inertia sensor 503, and acquire angular velocities for calculating a moving angle of the knee joint from at least a portion of the activated angular velocity meters. For example, the spasticity evaluation assisting apparatus may acquire a first angular velocity measured by the first inertia sensor 501 at the thigh part and a second angular velocity measured by the second inertia sensor 503 at the shaft part.

When the first acceleration and the second acceleration are acquired, the spasticity evaluation assisting apparatus may calculate an angle of the knee joint using a total acceleration obtained by adding the first acceleration to the second acceleration. For example, the spasticity evaluation assisting apparatus may calculate a gradient relative to a ground based on a magnitude of the total acceleration with respect to a gravitational acceleration as the angle of the knee joint.

Also, when the first angular velocity and the second angular velocity are acquired, the spasticity evaluation assisting apparatus may calculate the angle of the knee joint using a total angular velocity obtained by adding the first angular velocity to the second angular velocity. For example, the spasticity evaluation assisting apparatus may calculate the angle of the knee joint by integrating the total angular velocity.

Figure 6:
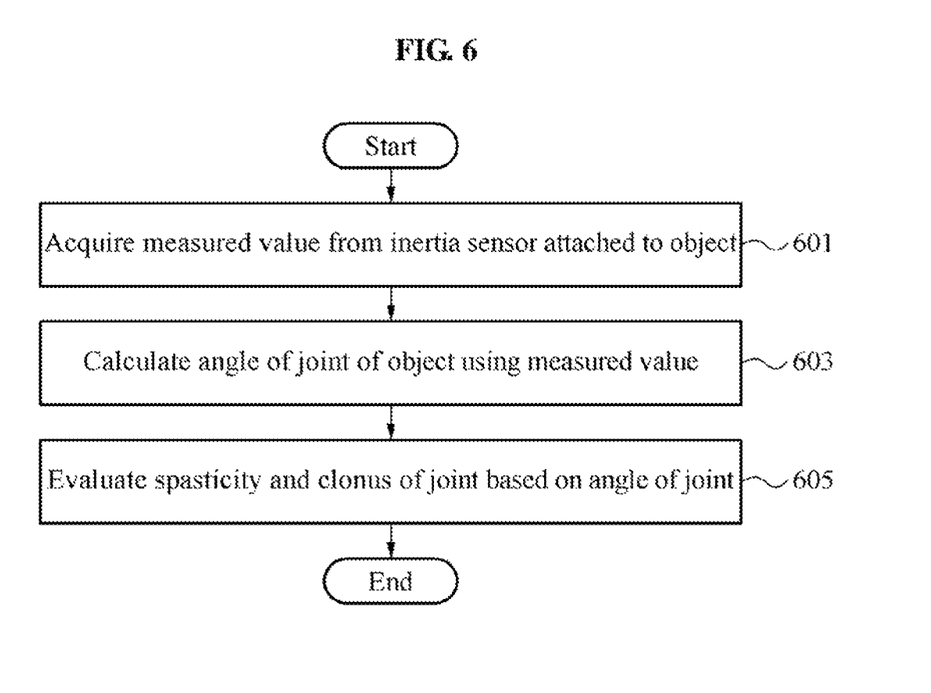
FIG. 6 is a flowchart illustrating a method of assisting spasticity evaluation using an inertia sensor according to an example embodiment.

FIG. 6 is a flowchart illustrating a method of assisting spasticity evaluation using an inertia sensor according to an example embodiment.

Referring to FIG. 6, in operation 601, a spasticity evaluation assisting apparatus may acquire a measured value from an inertia sensor attached to an object.

The spasticity evaluation assisting apparatus may acquire an acceleration from an acceleration meter included in the inertia sensor and acquire an angular velocity from an angular velocity meter included in the inertia sensor.

When the object is in a quasi-static state, the spasticity evaluation assisting apparatus may acquire the acceleration from the acceleration meter included in the inertia sensor. When the object is in a dynamic state, the spasticity evaluation assisting apparatus may acquire the angular velocity from the angular velocity meter included in the inertia sensor.

A plurality of inertia sensors may be respectively attached to predetermined portions spaced apart relative to the joint of the object to sense a movement of the object.

When the plurality of inertia sensors is attached to the object, the spasticity evaluation assisting apparatus may control acceleration meters or angular velocity meters included in the plurality of inertia sensors to acquire measured values from the plurality of inertia sensors. Specifically, the spasticity evaluation assisting apparatus may activate the acceleration meters included in the plurality of inertia sensors and acquire accelerations for calculating a stop angle of the joint from at least a portion of the activated acceleration meters. Also, the spasticity evaluation assisting apparatus may activate the angular velocity meters included in the plurality of inertia sensors and acquire angular velocities for calculating a moving angle of the joint from at least a portion of the activated angular velocity meters.

In this example, the spasticity evaluation assisting apparatus may determine that the object is in a quasi-static state when all movements sensed by the plurality of inertia sensors are less than a set value, and determine that the object is in the dynamic state when a movement sensed by one of the plurality of inertia sensors is greater than or equal to the set value. Here, the spasticity evaluation assisting apparatus may determine that the object is in the quasi-static state when a variation in each of the acceleration and the angular velocity is less than a first set value, for example, when little variation is present. Also, the spasticity evaluation assisting apparatus may determine that the object is in the dynamic state when the variation in each of the acceleration and the angular velocity is greater than or equal to a first set value, for example, when the variation is relatively large.

In operation 603, the spasticity evaluation assisting apparatus may calculate an angle of a joint of the object using the measured value acquired from the inertia sensor.

In this example, in response to a determination that the object is in the quasi-static state, the spasticity evaluation assisting apparatus may calculate the angle of the joint of the object based on the acceleration acquired by the acceleration meter included in the inertia sensor. In response to a determination that the object is in the dynamic state, the spasticity evaluation assisting apparatus may calculate the angle of the joint of the object based on the angular velocity acquired from the angular velocity meter included in the inertia sensor.

Also, when the acquired measured value is the acceleration, the spasticity evaluation assisting apparatus may calculate a gradient relative to a ground based on a magnitude of the acceleration with respect to a gravitational acceleration as the angle of the joint. When the acquired measured value is the angular velocity, the spasticity evaluation assisting apparatus may calculate the angle of the joint by integrating the angular velocity.

In operation 605, the spasticity evaluation assisting apparatus may evaluate a spasticity and a clonus of the joint based on the angle of the joint.

For example, the spasticity evaluation assisting apparatus may evaluate the spasticity and the clonus by obtaining at least one of a sum of stop angles calculated when the object is in the quasi-static state and a sum of moving angles calculated when the object is in the dynamic state.

The spasticity evaluation assisting apparatus may provide medical care information, for example, information on medication with Baclofen and Botulinum toxin injection based on an evaluation result of the spasticity and the clonus.

Also, the spasticity evaluation assisting apparatus may provide a real-time visual biofeedback by displaying a joint angular velocity obtained by summating the acquired angular velocities on a screen.

According to an aspect of the present embodiments, an angle of a joint of an object may be calculated based on a measured value, for example, an acceleration and an angular velocity using an inertia sensor attached to the object, and a spasticity and a clonus of the joint may be evaluated based on the angle of the joint. Through this, the angle of the joint may be accurately acquired based on objective numerical values and thus, a relatively high reliability may be achieved in a spasticity evaluation based on the angle of the joint.

Also, the acceleration may be acquired by an acceleration meter included in the inertia sensor and the angular velocity may be acquired by an angular velocity meter included in the inertia sensor. When a variation in each of the acceleration and the angular velocity is less than a first set value, for example, when little variation is present, the object may be determined to be in a quasi-static state, and the angle of the joint may be calculated based on the acceleration acquired by the acceleration meter. When the variation in each of the acceleration and the angular velocity is greater than or equal to a second set value, for example, the variation is relatively large, the object may be determined to be in a dynamic state, and the angle of the joint may be calculated based on the angular velocity acquired by the angular velocity meter. Thus, the angle of the joint may be accurately acquired based on objective numerical values acquired from the inertia sensor irrespective of a state of the object.

According to an aspect, it is possible to calculate an angle of a joint of an object based on a measured value, for example, an acceleration and an angular velocity using an inertia sensor attached to the object and evaluate a spasticity and a clonus of the joint based on the angle of the joint, thereby acquiring the angle of the joint accurately based on objective numerical values.

According to another aspect, it is possible to provide a visual biofeedback on an angular velocity of a joint based on a movement of the joint in real time, thereby achieving a relatively high reliability in a spasticity evaluation based on the angle of the joint. For example, the angular velocity may be verified based on the movement of the joint in real time using an angular velocity meter of an inertia sensor. Through this, objective data on a velocity may be provided, which may enhance reliability on the evaluation.

According to still another aspect, it is possible to calculate an angle of a joint of an object based on an acceleration acquired by an acceleration meter included in an inertia sensor when the object is in a quasi-static state and based on angular velocity acquired by an angular velocity meter included in the inertia sensor when the object is in a dynamic state, thereby acquiring the angle of the joint accurately based on objective numerical values acquired from the inertia sensor irrespective of a state of the object.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for assisting spasticity evaluation using a plurality of inertia sensors attached to an object and spaced apart relative to a joint of the object, each inertia sensor including an accelerometer and a gyroscope, the object having a quasi-static state when all movements sensed in the plurality of inertia sensors are less than a set value, and the object having a dynamic state when a movement sensed by one of the plurality of inertia sensors is greater than or equal to the set value, the apparatus comprising:

an acquirer configured to, during a quasi-static state of an object, acquire accelerations from accelerometers included in a plurality of inertia sensors, and configured to, during a dynamic state of the object, acquire angular velocities from the gyroscopes;

a calculator configured to calculate a gradient relative to a ground based on a magnitude of a sum of the accelerations with respect to a gravitational acceleration as an angle of the joint of the object in the quasi-static state, and calculate the angle of the joint of the object in the dynamic state by integrating the angular velocities; and a processor configured to,
evaluate a spasticity and a clonus of the joint based on the angle of the joint of the object in the quasi-static state and the angle of the joint of the object in the dynamic state, and
provide a visual biofeedback in real time by displaying a joint angular velocity obtained by summing the acquired angular velocities to allow a velocity adjustment while the angle of the joint of the object is measured.

2. The apparatus of claim 1, further comprising:
a determiner configured to determine when the object is in the quasi-static state and when the object is in the dynamic state.

3. The apparatus of claim 2, wherein
the acquirer is configured to activate the accelerometers included in the plurality of inertia sensors in response to the object being in the quasi-static state, and
the acquirer is configured to activate gyroscopes included in the plurality of inertia sensors in response to the object being in the dynamic state.

4. The apparatus of claim 1, wherein the processor is configured to evaluate the spasticity and the clonus by obtaining at least one of a sum of stop angles of the joint calculated when the object is in the quasi-static state and a sum of moving angles of the joint calculated when the object is in the dynamic state.

5. The apparatus of claim 1, wherein the processor is configured to provide medical care information based on an evaluation result of the spasticity and the clonus.

6. An apparatus for assisting spasticity evaluation, the apparatus comprising:
a plurality of inertia sensors attached to an object to be spaced apart relative to a joint of the object, each of the plurality of inertia sensors including an accelerometer to measure an acceleration and a gyroscope to measure an angular velocity based on a movement of the object, the object having a quasi-static state when all movements sensed in the plurality of inertia sensors are less than a set movement value, and the object having a dynamic state when a movement sensed by one of the plurality of inertia sensors is greater than or equal to the set movement value; and
a processor configured to calculate,
a joint velocity by summing angular velocities obtained from gyroscopes included in the plurality of inertia sensors with the object in the dynamic state, and
a joint angle of the object in the quasi-static state based on accelerations measured by accelerometers included in the plurality of inertia sensors, and the joint angle of the object in the dynamic state based on the angular velocities measured by the gyroscopes,
the processor further configured to display, on a screen, evaluation information of a spasticity and a clonus of the joint based on the angle of the joint of the object in the quasi-static state and the angle of the joint of the object in the dynamic state, and display the calculated joint velocity as real time visual biofeedback to allow a velocity adjustment while the angle of the joint of the object is measured, wherein the processor is configured to calculate the angle of the joint of the object in the quasi-static state based on a gradient relative to a ground based on a magnitude of a sum of the accelerations measured by the plurality of inertia sensors with respect to a gravitational acceleration and display a calculation result on the screen, and configured, to calculate the angle of the joint of the object in the dynamic state by integrating the angular velocities measured by the plurality of inertia sensors and display an integration result on the screen.

7. The apparatus of claim 6, wherein when the joint velocity reaches a set velocity value, the processor is configured to display whether the joint velocity succeeds in reaching the set velocity value on the screen.

8. The apparatus of claim 6, wherein the processor is configured to obtain at least one of a sum of stop angles of the joint calculated when the object is in the quasi-static state and a sum of moving angles of the joint calculated when the object is in the dynamic state, and display a summation result on the screen.

* * * * *